United States Patent [19]

Molloy

[11] 4,096,173

[45] Jun. 20, 1978

[54] CHLORINATED 1-AMINOINDANE N-METHYL TRANSFERASE INHIBITORS

[75] Inventor: Bryan B. Molloy, Indianapolis, Ind.

[73] Assignee: Eli Lilly and Company, Indianapolis, Ind.

[21] Appl. No.: 782,280

[22] Filed: Mar. 28, 1977

[51] Int. Cl.$^2$ .............................................. C07C 87/60
[52] U.S. Cl. ........................... 260/501.1; 260/501.21; 260/566 R; 260/578; 260/590 FA; 424/316; 424/330
[58] Field of Search ................. 260/578, 501.1, 501.21

[56] References Cited

U.S. PATENT DOCUMENTS

| | | | |
|---|---|---|---|
| 3,060,091 | 10/1962 | Witkin | 260/578 UX |
| 3,637,740 | 1/1972 | Sarges | 260/578 X |
| 3,919,316 | 11/1975 | Molloy | 260/578 |

OTHER PUBLICATIONS

Protiva et al., "Chemical Abstracts", vol. 60, pp. 1716–1717 (1964).

*Primary Examiner*—Robert V. Hines
*Attorney, Agent, or Firm*—James L. Rowe; Arthur R. Whale

[57] ABSTRACT

4-Chloro and 4,5-, 5,6- and 6,7-dichloro-1-aminoindanes, useful as inhibitors of norephineprine N-methyl transferase.

8 Claims, No Drawings

CHLORINATED 1-AMINOINDANE N-METHYL TRANSFERASE INHIBITORS

BACKGROUND OF THE INVENTION

5-Chloro-1-indanylamine (also named as 5-chloro-1-aminoindane) is disclosed in *Chem. Abstr.*, 60, 1716g (1964). This compound, as well as others disclosed in that publication, are stated to be anti-allergic, anti-spasmodic and local anesthetic drugs.

U.S. Pat. No. 3,988,339 discloses tetrahydroisoquinoline compounds useful as phenylethanolamine N-methyl transferase inhibitors (PNMT inhibitors), which isoquinolines may contain 1 or 2 chlorines in addition to various other permitted groupings in the phenyl ring of the tetrahydroisoquinoline ring system.

U.S. Pat. No. 3,919,316 discloses a series of 2-amino-dichlorotetralines, stated to be inhibitors of various enzyme ststems including specifically PNMT.

U.S. Pat. No. 3,637,740 discloses a group of tetrahydro-1-naphthylamines and substituted-1-aminoindanes useful as psycotherapeutic agents. Whereas chlorine is a permissible substituent in the phenyl ring of these tetrahydro-1-naphthylamine or 1-aminoindane derivatives, there is no disclosure therein of compounds which have only a chlorine substituent. For instance, Example I, discloses a 5-methoxy-8-chloro derivative. In addition, although a primary amine group is permissible in the 1-position of the tetrahydro naphthalene or indane ring system, the compounds actually disclosed are, in general, secondary and tertiary amines. Disclosure relevant to the preparation of 1-aminoindanes begins with the Example XXVII. Here again, the phenyl ring of the indane ring system is substituted with both a methoxy and a chlorine, and the final product is an N,N-dimethyl derivative. The Table at the top of column 14 discloses only 2 primary amines, both of the 1-aminoindane series, and these have respectively an OH in the 4-position and an acetyl in the 7-position of the phenyl ring.

There are many references to 1-aminoindane in the non-patent literature. 1-Aminoindane appears in Beilstein, *Hanbuch der Organ. Chem*, Bd XII, Syst. No. 1709 pg. 1191. Of particular interest is the reference appearing in *Chem. Abstr.* 62, 1616d (1965) which refers to 1-aminoindane derivatives valuable as anti-depressant and psychostimulating agents. The compounds in question are, in general, N-substituted 1-aminoindanes. Horn and Schenider, publishing in *J. Pharm. Exp. Ther*, 180, 523–30 (1972), state that 2-aminoindane is a better inhibitor of catechol amine uptake than 1-aminoindane.

2-Aminoindane can be looked upon as a rigid confromational analog of amphetamine and 1-aminoindane can be looked upon as a rigid conformational analog of benzylamine.

Nothing in the above-cited literature would suggest that selected chlorinated 1-aminoindanes would have unexpectedly high activity as inhibitors of N-methyl transferase.

SUMMARY OF THE INVENTION

This invention provides the following chlorinated 1-aminoindanes: 4-chloro-1-aminoindane, 4,5-dichloro-1-aminoindane, 5,6-dichloro-1-aminoindane and 6,7-dichloro-1-aminoindane. Pharmaceutically-acceptable acid addition salts of the above chlorinated 1-aminoindanes are also included within the scope of this invention.

The compounds of this invention are enzyme inhibitors, specifically inhibitors of norephineprine N-methyl transferase, previously referred to as PNMT (phenylethanolamine N-methyl transferase). A particularly active enzyme-inhibiting group of chlorinated 1-aminoindanes are those containing two vicinal chlorine atoms in the benzene ring of the indane molecule as represented by the following formula

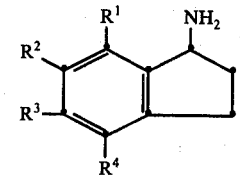

wherein two of $R^1$, $R^2$, $R^3$ and $R^4$ are vicinal chlorine atoms and the other two are hydrogen. Pharmaceutically-acceptable acid addition salts of the above dichlorinated indanes are also particularly useful.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyro-sulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

1-Aminoindane, represented by the formula

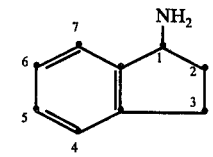

contains an asymmetric carbon atom, carbon atom 1. 1-Aminoindane is ordinarily prepared as a racemate but this racemate has been resolved into its dl components. This invention provides 4-chloro, 4,5-dichloro, 5,6-dichloro, and 6,7-dichloro-1-aminoindane, either as a racemic mixtures or as pure optical antipodes having the ability to inhibit norephineprine N-methyl transferase.

The compounds of this invention are prepared from a suitably chlorinated 1-indanone using a mixture of ammonium acetate and sodium cyanoborohydride, in an inert solvent such as a lower alkanol, specifically methanol. The chlorinated 1-indanone starting materials are prepared by cyclizing a β-chlorophenyl (or dichlorophenyl) propionic acid with polyphosphoric acid. If the β-(chlorinated phenyl)propionic acid has a chlorine atom in a position ortho to the propionic acid side chain, the ring closure can proceed in only one direction; i.e., to the other (and unsubstituted) ortho position. However, if the chlorinated phenyl ring contains two "open" (unsubstituted by chlorine) ortho positions, the ring closure can take place on either ortho position and a mixture of isomeric 1-indanones may result. This isomer mixture must be separated by chromatography, fractional crystallization, etc. as is well known in the art, to prepare the pure chlorinated 1-indanone starting materials useful for preparing the compounds of this invention.

This invention is further illustrated by the following specific examples:

EXAMPLE 1

Preparation of 4-Chloro-1-Aminoindane

Following the procedure of *J. Am. Chem. Soc.*, 59, 394 (1937) and *Coll. Czech. Chem.*, 27, 2413 (1962), 55.4 g. of β-(o-chlorophenyl)propionic acid and about 550 g. of polyphosphoric acid were heated to 100° C. with stirring for one hour. The hot reaction mixture was poured into 2.5 l. of an ice-water mixture. The resulting aqueous layer was extracted twice with chloroform. The chloroform extracts were combined and washed, first with water and then with 2N aqueous sodium hydroxide solution followed by a wash with a saturated aqueous sodium chloride solution. The chloroform layer was separated, dried and decolorized. Evaporation of the chloroform yielded a tan solid comprising 4-chloro-1-indanone formed in the above reaction. The compound, after being recrystallized from a benzene-hexane solvent mixture, melted at 86°–90° C.; yield = 16.8 g.

Analysis Calc.: C, 64.88; H, 4.24; Cl, 21.28; Found: C, 65.13; H, 4.01; Cl, 21.59.

A reaction mixture was prepared in a 250 ml. round bottom flask equipped with magnetic stirrer and drying tube containing the following ingredients: 32.5 g. of ammonium acetate, 2.67 g. of sodium cyanoborohydride (NaBH$_3$CN), 70 ml. of tetrahydrofurane (THF), 60 ml. of methanol and 7 g. of 4-chloro-1-indanone. The reaction mixture was stirred at room temperature for about 48 hours. Thin-layer chromatography indicated only a trace of starting ketone remaining. The reaction mixture was cooled to below about 15° C. and acidified to pH = 2 with 12N aqueous hydrochloric acid. Volatile constituents were removed by evaporation in vacuo. The residue was taken up in water and the aqueous mixture extracted three times with ether. The ether extracts were discarded. The aqueous phase was then made basic with 5N aqueous sodium hydroxide and 4-chloro-1-aminoindane, formed in the above reaction, being insoluble in the alkaline layer separated and was extracted into ether. The ether layer was separated and the alkaline layer extracted twice more with ether. The ether extracts were combined, washed with saturated aqueous sodium chloride, and then dried. Evaporation of the ether in vacuo yielded 1.377 g. of an oily residue comprising 4-chloro-1-aminoindane. The hydrochloride salt was prepared by dissolving the residue in ether and passing gaseous hydrogenchloride through the ether solution. The resulting solid hydrochloride salt was separated by filtration. Recrystallization of the salt from a 3:1 isopropanol/ethyl acetate solvent mixture yielded 4-chloro-1-aminoindane hydrochloride melting above 250° C. (total yield = 641 mg.)

Analysis Calc.: C, 52.96; H, 5.43; N, 6.86; Cl, 34.74; Found: C, 53.13; H, 5.69; N, 6.68; Cl, 34.56.

The cyanoborohydride reduction can also be carried out in methanol above as a solvent.

EXAMPLE 2

Preparation of 5,6-Dichloro-1-Aminoindane

Following the procedure of Example 1, 70 g. of β-(3,4-dichlorophenyl)propionic acid were cyclized with 500 ml. of polyphosphoric acid to yield a mixture of 5,6-dichloro-1-indanone and 6,7-dichloro-1-indanone. The reaction mixture was poured over ice and extracted with ethyl acetate. The ethyl acetate layer was separated and the solvent removed by evaporation. A benzene solution of the ethyl acetate-soluble residue was chromatographed over silica with only small enrichment of the desired 5,6-dichloro-1-indanone. All solids obtained from evaporation of the chromatographic fractions were combined and dissolved in 750 ml. of boiling 95 percent ethanol. The ethanol solution was decolorized with charcoal and filtered. The solution volume was reduced to about 300 ml. and the 5,6-dichloro-1-indanone allowed to crystallize at 0° C. The solution was warmed to ambient temperature and filtered to yield 9.6 g. of a brown solid. VPC indicated that the crystalline material contained about 65 percent of the 5,6-dichloro isomer (weight = 9.36 g.). An additional 4.84 g. of solid were obtained by concentrating the mother liquor to a volume of about 200 ml. Fractional recrystallization from ethyl acetate of the two solid fractions eventually yielded 6.03 g. of 100 percent pure 5,6-dichloro-1-indanone melting at 147°–149° C.

Following the procedure of Example 1, 5,6-dichloro-1-indanone was reacted with ammonium acetate and sodium cyanoborohydride to yield 5,6-dichloro-1-aminoindane; yield = 670 mg. The crystalline compound was treated with 360 mg. of maleic acid in 25 ml. of isopropanol. The maleate salt crystallized and was separated by filtration. Recrystallization of the salt from a 1:3 isopropanol/ethyl acetate solvent mixture yielded 650 mg. of 5,6-dichloro-1-aminoindane maleate melting at 167°–170° C.

Analysis Calc.: C, 49.08; H, 4.12; N, 4.40; Cl, 22.29; Found: C, 49.31; H, 4.05; N, 4.47; Cl, 22.58.

EXAMPLE 3

Preparation of 6,7-Dichloro-1-Aminoindane

Following the procedure of Example 1, 6,7-dichloro-1-indanone isolated from the mother liquors which yielded 5,6-dichloro-1-indanone of the previous example, was reacted with ammonium acetate and sodium cyanoborohydride in methanol to yield 6,7-dichloro-1-aminoindane as the maleate salt melting at 152°–154° C.

Analysis Calc.: C, 49.08; H, 4.12; N, 4.40; Cl, 22.29; Found: C, 48.86; H, 4.12; N, 4.61; Cl, 21.01.

The NMR for this compound was consistent with the proposed structure; pKa = 3.3, 10.3.

EXAMPLE 4

Preparation of 4,5-Dichloro-1-Aminoindane

Following the procedure of Example 1, β-(2,3-dichlorophenyl)propionic acid was cyclized with polyphosphoric acid to yield 4,5-dichloro-1-indanone. Reaction of this compound with ammonium acetate and sodium cyanoborohydride in methanol yielded 4,5-dichloro-1-aminoindane which was converted to the maleate salt and the salt recrystallized from an isopropanol-ethyl acetate solvent mixture. Further recrystallization from a methanol-ethyl acetate solvent mixture yielded compound melting at 172°–174° C.

Analysis Calc.: C, 49.35; H, 4.30; N, 4.68; Cl, 22.59; Found: C, 49.02; H, 4.35; N, 4.61; Cl, 22.04.

The compounds of this invention, either in the form of the free base, or as a pharmaceutically-acceptable acid addition salt thereof, are enzyme inhibitors. In particular, as previously stated, they are inhibitors of norephineprine N-methyl transferase [PNMT or phenethanolamine N-methyl transferase—see Axelod, *J. Bio, Chem.*, 237, 1657 (1962)]. Compounds which inhibit the conversion of norephineprine to ephineprine, are capable of lowering a high ephineprine-norephineprine ratio in mammals, a physiological condition frequently associated with essential hypertension. The compounds of this invention are thus capable of ameliorating the ephineprine-norephineprine imbalance in essential hypertension, an important aspect of the treatment of this disease state. The effectiveness of the compounds as N-methyl transferase inhibitors has been measured in vitro using NMT from rabbit adrenals. By using a series of decreasing concentration of the inhibiting amine, usually starting with $1 \times 10^{-4}M$ continuing with $3 \times 10^{-5}M$, $1 \times 10^{-5}M$, etc., it was possible to determine a concentration at which the 50 percent inhibition of NMT was achieved. The negative reciprocal logarhithm ($pI_{50}$) of this number was also calculated as a useful index. Table 1, which follows, summarizes the information thus obtained; i.e., the determination of enzyme inhibition activity for the compounds of this invention. In the table, column 1 gives the name of the compound, column 2, the concentration at which 50 percent inhibition of NMT is obtained and column 3, the $pI_{50}$.

TABLE 1

| Name | 50 Inhibitory Concentration | $pI_{50}$ |
| --- | --- | --- |
| 4-Chloro-1-aminoindane hydrochloride | $7.57 \times 10^{-7}$ | 6.12 |
| 5,6-dichloro-1-aminoindane maleate | $2.95 \times 10^{-6}$ | 5.33 |
| 6,7-dichloro-1-aminoindane | $5.37 \times 10^{-6}$ | 5.22 |
| 4,5-dichloro-1-aminoindane | $2 \times 10^{-7}$ | 6.70 |

The compounds of this invention are used as NMT inhibitors, preferably in the form of an acid addition salt. These salts can be mixed with one or more standard pharmaceutical excipients and loaded into empty telescoping gelatin capsules or compressed into tablets. Aqueous solutions of these salts can be employed for parenteral administration, with an isotonic solution being particularly adapted for IV use.

I claim:

1. A compound selected from the group consisting of 4-chloro-1-aminoindane, 4,5-dichloro-1-aminoindane, 5,6-dichloro-1-aminoindane and 6,7-dichloro-1-aminoindane and pharmaceutically-acceptable acid addition salts thereof.

2. A compound according to claim 1, said compound being 4-chloro-1-aminoindane.

3. A compound according to claim 1, said compound being 4,5-dichloro-1-aminoindane.

4. A compound according to claim 1, said compound being 5,6-dichloro-1-aminoindane.

5. A compound according to claim 1, said compound being 6,7-dichloro-1-aminoindane.

6. The hydrochloride salt of the compound of claim 2.

7. The maleate salt of the compound of claim 3.

8. A compound of the formula

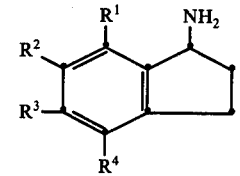

wherein two of $R^1$, $R^2$, $R^3$ and $R^4$ are vicinal chlorine atoms and two are hydrogen; and pharmaceutically-acceptable salts thereof.

* * * * *